United States Patent [19]

Post et al.

[11] 4,403,044

[45] Sep. 6, 1983

[54] PROCESS FOR CARRYING OUT CATALYTIC CONVERSIONS

[75] Inventors: Martin F. M. Post; Swan T. Sie, both of Amsterdam, Netherlands

[73] Assignee: Shell Oil Company, Houston, Tex.

[21] Appl. No.: 236,383

[22] Filed: Feb. 20, 1981

[30] Foreign Application Priority Data

Mar. 6, 1980 [NL] Netherlands ......................... 8001342

[51] Int. Cl.³ .......................... C07C 1/04; C07C 1/20; C07C 3/00
[52] U.S. Cl. .................................... 518/714; 518/713; 518/715; 585/408; 585/418; 585/322; 585/640
[58] Field of Search .............. 518/721, 715, 713, 714; 585/408, 418, 319, 322, 640, 310

[56] References Cited

U.S. PATENT DOCUMENTS

| | | | |
|---|---|---|---|
| 3,894,104 | 7/1975 | Chang et al. | 585/408 |
| 4,011,275 | 3/1977 | Zahner | 518/713 |
| 4,061,724 | 12/1977 | Grose et al. | 423/335 |
| 4,086,262 | 4/1978 | Chang et al. | 518/715 X |
| 4,138,442 | 2/1979 | Chang et al. | 518/702 |
| 4,188,336 | 2/1980 | Chang et al. | 518/714 |
| 4,208,305 | 6/1980 | Kouwenhoven | 518/715 X |
| 4,263,141 | 4/1981 | Möller et al. | 585/310 X |

OTHER PUBLICATIONS

Anderson et al., J. Catalysis, 58, 114 (1979).
Bibby et al., Nature, 280, 664 (1979).
Price et al., Nature, 292, 818 (1981).

*Primary Examiner*—Delbert E. Gantz
*Attorney, Agent, or Firm*—John M. Duncan; Ronald R. Reper

[57] ABSTRACT

A process for the manufacture and/or conversion of hydrocarbons comprises contacting as feed any of: a gaseous mixture of carbon monoxide and hydrogen, acyclic organic compounds, hydrocarbon compounds, and mixtures thereof, under conversion conditions with a catalyst comprising silicalite.

14 Claims, No Drawings

PROCESS FOR CARRYING OUT CATALYTIC CONVERSIONS

BACKGROUND OF THE INVENTION

The invention relates to a process for carrying out catalytic conversions in which a catalyst is used consisting at least partly of a crystalline silica.

In U.S. Pat. No. 4,061,724 granted to Union Carbide Corporation a novel crystalline silica is described. The crystalline silica, denominated silicalite, is characterized in having the following properties after calcining in air for 1 hour at 600° C.:

(1) Specific density at 25° C.: $1.70 \pm 0.05$ g/ml;
(2) Average refractive index: $1.39 \pm 0.01$;
(3) An X-ray powder diffraction pattern in which the six lines in Table A are the strongest lines.

TABLE A

| Radiation: Cu—K $d(Å)$ | Relative intensity (VS = very strong; S = strong) |
| --- | --- |
| 11.1 ± 0.2 | VS |
| 10.0 ± 0.2 | VS |
| 3.25 ± 0.07 | VS |
| 3.22 ± 0.07 | S |
| 3.76 ± 0.05 | S |
| 3.72 ± 0.05 | S |

(4) Crystals with an orthorhombic structure having the following unit cell parameters:

$$a = 20.05 \text{ Å}, b = 20.0 \text{ Å and } c = 13.4 \text{ Å}$$

(accuracy of each of these values $\pm 0.1$ Å)
(5) Pore diameter: about 6 Å;
(6) Pore volume: 0.18 ml/g.

The preparation of silicalite may be carried out by heating an aqueous mixture containing a silicon compound, alkylammonium or phosphonium ions ($R_4X^+$) and optionally alkali metal ions ($Me^+$) and having a pH between 10 and 14, until the crystalline silicalite precursor has formed, and subsequently separating the latter from the mother liquor, and washing, drying and calcining it. The alkylammonium or phosphonium ions may be introduced into the reaction mixture by incorporating into it tetraalkylammonium or phosphonium hydroxides or the salts derived from these compounds, or by forming the quaternary ions in situ, for instance by reaction of a tertiary alkylamine and an alkylhalogenide. Suitable silicon compounds are amorphous silicas and alkali metal silicates. In the preparation of the silicalite the various reaction components should be present in the following ratios, expressed in moles of the oxides per mole quaternary alkylammonium or phosphonium oxide ($R_4X)_2O$:
150–700 moles $H_2O$,
13–50 moles $SiO_2$,
0–6.5 moles $Me_2O$.

The preparation of the silicalite may very conveniently be carried out by heating the reaction mixture for 5 to 150 hours under autogenous pressure at a temperature between 100° and 250° C.

The uniform pore structure imparts form-selective molecular sieve properties to the silicalite. Thanks to the pore structure, silicalite can be used for separating p-xylene from mixtures with other $C_8$ aromatics. Silicalite can also be used for separating compounds containing quaternary carbon atoms from mixtures with other organic compounds. Silicalite has a very useful hydrophobic/organophilic characteristic which permits its use in selectively absorbing organic compounds from water.

The applicants have carried out an investigation concerning the use of silicalite for catalytic purposes. This investigation has shown that materials consisting at least partly of silicalite may be advantageously used as catalyst for carrying out a variety of catalytic conversions for the production, i.e., synthesis and/or conversion of hydrocarbon products.

SUMMARY OF THE INVENTION

The present patent application therefore relates to a process for the production of hydrocarbon products which comprises contacting a feed selected from (1) gaseous mixtures containing carbon monoxide and hydrogen, (2) acyclic organic compounds, (3) hydrocarbon compounds and (4) mixtures of these, in a contact zone at conversion conditions with a catalyst comprising silicalite and recovering a hydrocarbon product from said contact zone.

DESCRIPTION OF PREFERRED EMBODIMENTS

Silicalite has catalytic activity and can therefore as such be used as a catalyst. Silicalite can also be used as carrier for one or more catalytically active metal components. Very suitable catalysts for a variety of processes are catalysts containing one of the following metals or metal combinations on silicalite as the carrier: nickel, copper, zinc, cadmium, platinum, palladium, nickel-tungsten, cobalt-molybdenum, nickel-molybdenum, zinc-palladium, zinc-copper and zinc-rhenium. Deposition of the metals on silicalite may be effected in a conventional way, for instance by impregnation. To increase the activity, selectively and/or stability of the catalysts, promoters may be incorporated into them, such as halogen, magnesium, phosphorus, arsenic and antimony.

When silicalite is used for catalytic purposes, the material should, as a rule, be available in the form of particles with a diameter of 0.5–5 mm. In the procedure described hereinbefore silicalite is obtained in the form of a fine powder. Silicalite may be shaped into particles of a larger size, for instance by pressing. During the shaping, silicalite may be combined with a binder material such as kaolin or bentonite. When silicalite is combined with a binder material, any mixing ratio may in principle be used. For the sake of brevity, catalysts consisting at least partly of silicalite will in this patent application be denominated "catalysts according to the invention."

Although the catalysts according to the invention have a long life, they have to be regenerated from time to time. This can simply be done by burning.

Among the processes for which catalysts according to the invention may be used are:
(1) Catalytic cracking of heavy hydrocarbon oils for the preparation of light hydrocarbon oil distillates;
(2) preparation of isoparaffins by isomerization of n-paraffins;
(3) hydrodesulphurization of hydrocarbon oil distillates;
(4) conversion of naphthenes into aromatics;
(5) polymerization of olefins for the preparation of polyolefins;

(6) hydrocracking of heavy hydrocarbon oils for the preparation of light hydrocarbon oil distillates, such as the conversion of gas oil into gasoline;

(7) hydrocracking of heavy hydrocarbon oils for the preparation of lubricating oils with a high viscosity index;

(8) improving the light and oxidation stability of lubricating oils;

(9) improving the octane number of gasoline;

(10) preparation of olefins from lower alcohols and/or ethers;

(11) preparation of olefinic gasoline with a low aromatics content from lower olefins or mixtures thereof with lower paraffins;

(12) hydrodewaxing of hydrocarbon oils such as lubricating oil and fuel for jet engines;

(13) transalkylation of alkyl-substituted aromatics, such as the preparation of ethylebenzene from a mixture of benzene and diethylbenzene;

(14) alkylation of aromatics such as the preparation of ethylbenzene from benzene and ethylene.

Catalysts according to the invention are very suitable for use in the following processes:

(1) Catalytic dewaxing of gas oil for improving the cloud point;

(2) preparation of p-xylene by isomerization of other $C_8$ aromatics;

(3) preparation of p-xylene by methylation of toluene with, for instance, methanol, methyl chloride or dimethyl ether;

(4) preparation of p-xylene by disproportionation of toluene.

Although catalysts according to the invention can be successfully used for each of the above processes, the great importance of these catalysts lies in another domain. It has been found that these catalysts are preeminently suitable for the preparation of aromatic hydrocarbons from acyclic organic compounds. As starting material for the preparation of these aromatics, organic compounds of a variety of classes are eligible, such as alcohols, ethers, olefins, diolefins, paraffins, aldehydes, ketones and esters. It has been found that these catalysts not only have the property of forming aromatics from organic compounds with six or more carbon atoms in the molecule, such as hexadecene, but are surprisingly capable of forming, in high yield, aromatics from organic compounds with fewer than six carbon atoms in the molecule, such as methanol, ethanol and propene. Another surprising property of the catalysts according to the invention is that, when used in the above-mentioned preparation of aromatics, they yield a product in which the aromatics contain substantially at least six and at most ten carbon atoms, irrespective of whether the preparation was started from organic compounds with six or more carbon atoms, or from organic compounds with fewer than six carbon atoms. The latter property of the catalysts according to the invention is considered to be very important, since aromatic compounds with 6-10 carbon atoms in the molecule are excellently suited for use as gasoline components.

The preparation of aromatics using catalysts according to the invention may be started from a certain acyclic organic compound, such as methanol or propylene, and from a mixture consisting substantially of acyclic organic compounds. The aromatization process according to the invention is very suitable for the preparation of aromatics from methanol and for increasing the octane number of gasolines such as straight-run gasolines and gasolines obtained in the hydrocracking, thermal cracking and catalytic cracking of mineral oil fractions.

The preparation of aromatic hydrocarbons from aliphatic and/or cycloaliphatic hydrocarbons is carried out by contacting the feed under aromatization conditions with a catalyst according to the invention. Examples of suitable starting materials for the preparation of aromatics are ethylene, propylene, butylene, propane, butane, pentane, hexane, methylpentane, methylcyclopentane, udex raffinates, straight-run gasoline fractions, pyrolysis gasoline fractions, and products obtained in the hydrocarbon synthesis according to Fischer-Tropsch.

In addition to aliphatic and cycloaliphatic hydrocarbons, hydrocarbons containing an heteroatom, such as an oxygen, halogen, sulphur or nitrogen atom may also be used as the feed for the aromatization process according to the invention. Examples of suitable compounds of this type are: methanol, ethanol, isopropanol, 2-ethylhexanol, mixtures of oxo alcohols, mixtures of pentanols, mixtures of methanol and propylene, methyl mercaptan, dimethyl ether, tri-n-butylamine, methyl formate, acetic acid, acetone, propionaldehyde, cyclopentanone, n-butyl formate, n-propyl acetate and caproic acid.

The aromatization process according to the invention is very suitable for the preparation of an aromatic hydrocarbon mixture from a $C_4^-$ monoolefin or from a hydrocarbon mixture consisting of more than 75% w to $C_4^-$ monoolefins. It is preferred to start from a $C_3$ or $C_4$ monoolefin or from a hydrocarbon mixture consisting substantially of one or more of these monoolefins. A very suitable feed is the hydrocarbon mixture consisting substantially of $C_3$ and/or $C_4$ monoolefins that is obtained as by-product in the catalytic or thermal cracking of hydrocarbons, and particularly in the thermal cracking of hydrocarbons for the preparation of ethylene.

The aromatization process according to the invention is also very suitable for the preparation of an aromatic hydrocarbon mixture from a $C_4$ paraffin or from a hydrocarbon mixture consisting of more than 75% w $C_4^-$ paraffins and of more than 50% w $C_4$ paraffins. It is preferred to start from a hydrocarbon mixture consisting of more than 75% w $C_4$ paraffins. A very suitable feed is the hydrocarbon mixture consisting substantially of $C_3$ and $C_4$ paraffins that is obtained as by product in the production of mineral oil.

The aromatization process according to the invention is also very suitable for the preparation of an aromatic hydrocarbon mixture from a feed consisting of one or more aliphatic alcohols and/or ethers. The preferred starting material is methanol and/or dimethyl ether.

The aromatization process according to the invention is particularly suitable for application to hydrocarbons and/or oxygen-containing hydrocarbons obtained in the conversion of a mixture of carbon monoxide and hydrogen. The conversion of an $H_2/CO$ mixture into an aromatic hydrocarbon mixture using a catalyst according to the invention may be carried out in one step or in two steps. In the two-step process an $H_2/CO$ mixture is contacted in the first step with a catalyst containing one or more metal components with catalytic activity for the conversion of an $H_2/CO$ mixture into hydrocarbons and/or oxygen-containing hydrocarbons. In the second step the product thus obtained is converted into an aromatic hydrocarbon mixture by contacting it under aromatization conditions with a catalyst according to the invention. In the one-step process an $H_2/CO$ mixture is contacted with a bifunctional catalyst containing, in addition to silicalite, one or more metal components with catalytic activity for the conversion of an $H_2/CO$ mixture into hydrocarbons and/or oxygen-containing hydrocarbons. The process is preferably carried out as a one-step process. If the $H_2/CO$ mixture that is used as the feed in the aromatization process according to the invention has an $H_2/CO$ molar ratio of less than 1.0 (such $H_2/CO$ are obtained, inter alia, in the high-temperature steam gasification of coal), the aromatization process is preferably carried out as a one-step process by contacting the gas with a trifunctional catalyst containing one or more metal components with catalytic activity for the conversion of an $H_2/CO$ mixture into hydrocarbons and/or oxygen-containing hydrocarbons, one or more metal components with catalytic activity for the water gas shift reaction, and silicalite. The ratio in which the three catalytic functions are present in the catalyst may vary within wide limits and is predominantly determined by the activity of each of the catalytic functions. When in the aromatization process according to the invention a trifunctional catalyst is used for converting an $H_2/CO$ mixture with an $H_2/CO$ molar ratio of less than 1.0, the intention is that as much as possible of the acyclic hydrocarbons and/or oxygen-containing hydrocarbons formed under the influence of a first catalytic function, is converted under the influence of a second catalytic function into an aromatic hydrocarbon mixture substantially boiling in the gasoline range, while as much as possible of the water than is released in the conversion of the $H_2/CO$ mixture into hydrocarbons and/or in the conversion of oxygen-containing hydrocarbons into an aromatic hydrocarbon mixture, reacts under the influence of a third catalytic function with the CO present in excess in the $H_2/CO$ mixture, forming an $H_2/CO_2$ mixture.

Although the trifunctional catalysts that are used in the aromatization process according to the invention are described in this patent application as catalysts containing one or more metal components with catalytic activity for the conversion of an $H_2/CO$ mixture into hydrocarbons and/or oxygen-containing hydrocarbons and one or more metal components with catalytic activity for the water gas shift reaction, this does not mean that separate metal components each having one of the two functions should always be present in the catalysts. It has been found that metal components and combinations of metal components with catalytic activity for the conversion of an $H_2/CO$ mixture into substantially oxygen-containing hydrocarbons as a rule also have sufficient catalytic activity for the water gas shift reaction, so that incorporation of one metal component or one combination of metal components into the catalysts will then suffice. Examples of such metal components are metals selected from the group formed by zinc, copper and chromium. When trifunctional catalysts containing these metals are used in the aromatization process according to the invention, preference is given to catalysts containing combinations of at least two of these metals, for instance the combinations zinc-copper, zinc-chromium or zinc-copper-chromium. Particular preference is given to a trifunctional catalyst containing in addition to silicalite the metal combination zinc-chromium. Metal components and combinations of metal components with catalytic activity for the conversion of an $H_2/CO$ mixture into substantially hydrocarbons have, as a rule, no or insufficient activity for the water gas shift reaction. Therefore, when such metal components are used in the catalysts, one or more separate metal components with catalytic activity for the water gas shift reaction should be incorporated.

The trifunctional catalysts that are used in the aromatization process according to the invention are preferably composed of two or three separate catalysts, which will be designated, for the sake of convenience, as catalysts X, Y and Z. Catalyst X is the one containing the metal components with catalytic activity for the conversion of an $H_2/CO$ mixture into hydrocarbons and/or oxygen-containing hydrocarbons. Catalyst Y is silicalite. Catalyst Z is the one containing the metal components with catalytic activity for the water gas shift reaction. As explained hereinbefore, the use of a Z-catalyst may be omitted in certain cases.

If as the X-catalyst a catalyst is used that is capable of converting an $H_2/CO$ mixture into substantially oxygen-containing hydrocarbons, preference is given to a catalyst capable of converting the $H_2/CO$ mixture into substantially methanol and/or dimethyl ether. For the conversion of an $H_2/CO$ mixture into substantially methanol very suitable catalysts are those containing the above-mentioned metal combinations. If desired, the said metal combinations may be deposited on a carrier. By incorporating an acid function into these catalysts, for instance by depositing the metal combination on an acid carrier, the $H_2/CO$ mixture can be converted not only into methanol, but also for a considerable part into dimethyl ether.

X-catalysts with activity for the conversion of an $H_2/CO$ mixture into substantially hydrocarbons are known as Fischer-Tropsch catalysts. As a rule, these catalysts contain one or more metals of the iron group or rutherium together with one or more promotors to increase the activity and/or selectivity, and sometimes a carrier material such as kieselguhr. If in the aromatization process according to the invention, with an $H_2/CO$ mixture as the starting material, use is made of a catalyst combination in which catalyst X is a Fischer-Tropsch catalyst, preference is given to an iron or cobalt catalyst, in particular such a catalyst which has been prepared by impregnation. Examples of suitable Fischer-Tropsch catalyst, preference is given to an iron or cobalt catalyst, in particular such a catalyst which has been prepared by impregnation. Examples of suitable Fischer-Tropsch catalysts are catalysts prepared by impregnation containing either iron, potassium and copper, or cobalt, thorium and magnesium on silica as the carrier. If desired, it is also possible to use in the aromatization process according to the invention, with an $H_2/CO$ mixture as the starting material, catalyst combinations containing an X-catalyst capable of converting an $H_2/CO$ mixture into a mixture containing hydrocarbons and oxygen-containing hydrocarbons in comparable amounts. As a rule, such a catalyst also has sufficient catalytic activity for the water gas shift reaction, so that the use of a Z-catalyst in the combination can be omitted. An example of an X-catalyst of this type is an iron-chromium oxide catalyst. If desired, it is also possible to use in the aromatization process according to the invention, with an $H_2/CO$ mixture as the starting material, catalyst combinations containing two or more catalysts of the X-type, for instance in addition to a first catalyst of the X-type capable of converting an $H_2/CO$ mixture into substantially hydrocarbons, a second catalyst of the X-type capable of converting an $H_2/CO$ mixture into substantially oxygen-containing hydrocarbons.

Z-catalysts capable of converting an $H_2O/CO$ mixture into an $H_2/CO_2$ mixture are known in the literature as CO-shift catalysts. A very suitable Z-catalyst for the present purpose is a catalyst containing zinc and copper.

The conversion of an $H_2/CO$ mixture into an aromatic hydrocarbon mixture according to the invention is preferably carried out at a temperature of from 200° to 500° C. and in particular of from 300° to 450° C., a pressure of from 1 to 150 bar and in particular of from 5 to 100 bar and a space velocity of from 50 to 5000 and in particular of from 300 to 3000 Nl gas/l catalyst/h. In the preparation of an aromatic hydrocarbon mixture according to the invention, starting from an $H_2/CO$ mixture with an $H_2/CO$ molar ratio of less than 1.0, it is preferred to use an $H_2/CO$ mixture prepared by high-temperature steam gasification of coal.

The aromatization process according to the invention is also very suitable for the preparation of p-xylene from lower hydrocarbons such as propane, propylene, butanes, butylenes, n-hexane, cyclopentane and methylcyclopentane.

Below a number of processes are listed which are carried out using a catalyst according to the invention:

(1) A process for the preparation of liquid hydrocarbons from coal, in which:
  (a) the coal is converted by gasification into a mixture of carbon monoxide and hydrogen,
  (b) the mixture of carbon monoxide and hydrogen is converted into an aromatic hydrocarbon mixture using a catalyst according to the invention,
  (c) from the aromatic hydrocarbon mixture as isobutane-containing gaseous fraction and an aromatic liquid fraction boiling in the gasoline range are separated,
  (d) the isobutane-containing gaseous fraction is converted by alkylation into a product from which a fraction boiling in the gasoline range is separated, and
  (e) the two fractions obtained according to (c) and (d) boiling in the gasoline range are mixed.

(2) A process for the preparation of an aromatic hydrocarbon mixture, in which a mixture of aliphatic oxygen-containing hydrocarbons with the overall formula $C_nH_mO_p$, which mixture consists for a predominant molar part of one or more compounds for which $$\frac{m-2p}{n}$$

is greater than 1, and for the rest of one or more compounds for which $$\frac{m-2p}{n}$$

is at most 1, is contacted at elevated temperature with a catalyst according to the invention.

(3) A process for the preparation of an aromatic hydrocarbon mixture from natural gas, in which
  (a) the natural gas is converted into synthesis gas,
  (b) the synthesis gas is converted into an aromatic hydrocarbon mixture using a catalyst according to the invention,
  (c) from the aromatic hydrocarbon mixture a $C_2^-$ fraction, an isobutane-containing gaseous fraction and an aromatic liquid fraction boiling in the gasoline range are separated,
  (d) the $C_2^{-0}$ fraction is recycled to step (a) of the process,
  (e) the isobutane-containing gaseous fraction is converted by alkylation into a product from which a fraction boiling in the gasoline range is separated, and
  (f) the two fractions obtained according to (c) and (e) boiling in the gasoline range are mixed.

(4) A process for the preparation of an aromatic hydrocarbon mixture from methanol, which process is carried out in two steps, dimethyl ether being prepared in the first step by contacting methanol at elevated temperature with a dehydration catalyst, and an aromatic hydrocarbon mixture being prepared in the second step by contacting dimethyl ether originating from the first step at elevated temperature with a catalyst according to the invention.

(5) A process for upgrading a product obtained in the hydrocarbon synthesis according to Fischer-Tropsch, in which from the product a light fraction is separated consisting substantially of components boiling in and/or below the gasoline range and/or a heavy fraction consisting substantially of components boiling above the gasoline range, and in which an aromatic motor gasoline is prepared from the light fraction and/or a fuel with a low pour point from the heavy fraction by contacting the fraction concerned at elevated temperature with a catalyst according to the invention.

(6) A process for the preparation of a hydrocarbon mixture rich in aromatics from a hydrocarbon mixture poor in aromatics boiling in the gasoline range, in which the hydrocarbon mixture poor in aromatics is catalytically reformed and in which at least part of the reformate is contacted at elevated temperature with a catalyst according to the invention.

(7) A process for the preparation of gasoline, in which a hydrocarbon mixture boiling above the gasoline range is cracked using a catalyst mixture containing components A and B, in which a fraction boiling in the gasoline range is separated from the cracked product, in which catalyst component A is a crystalline aluminum silicate zeolite with a pore diameter of more than 9 A, and in which catalyst component B is silicalite.

(8) A process for the preparation of a hydrocarbon mixture boiling in the gasoline range and ethylene, in which
  (a) a mixture of carbon monoxide and hydrogen is converted into an aromatic hydrocarbon mixture using a catalyst according to the invention,
  (b) a liquid fraction boiling in the gasoline range and a gaseous fraction are separated from the crude reaction product, and
  (c) the gaseous fraction is converted by pyrolysis into a product containing ethylene.

(9) A process for the preparation of a hydrocarbon mixture boiling in the gasoline range, in which
  (a) a mixture of carbon monoxide and hydrogen is converted into an aromatic hydrocarbon mixture using a catalyst according to the invention,
  (b) a gaseous fraction containing propane and/or butane and a liquid fraction boiling in the gasoline range are separated from the aromatic hydrocarbon mixture, (c) the gaseous fraction is subjected to partial dehydrogenation or partial oxidation, (d) the olefinic or oxygen-containing product obtained is converted into an aromatic hydrocarbon mixture using a catalyst according to the invention, and (e) a fraction boiling in the gasoline range is separated from the aromatic hydrocarbon mixture obtained according to (d).

(10) A process for the preparation of a gaseous fuel with a colorific value of at least 30 MJ/m$^3$, in which (a) a mixture of carbon monoxide and hydrogen with an H$_2$/CO molar ratio smaller than 1 is converted into a hydrocarbon-containing reaction mixture by contacting the H$_2$/CO mixture with a mixture of two catalysts of which one contains zinc and/or copper and has the capability of catalyzing the conversion of an H$_2$/CO mixture into acyclic oxygen-containing hydrocarbons and the other is a catalyst according to the invention, (b) from the hydrocarbon-containing reaction mixture the C$_4$$^-$ fraction is separated, (c) the gaseous fuel from the C$_4$$^-$ fraction is prepared by removing at least part of the CO$_2$ present therein, and (d) the conditions for the preparation of the hydrocarbon-containing reaction mixture are chosen such that the conversion of the H$_2$/CO mixture is at least 70% w.

(11) A process for the preparation of an aromatic hydrocarbon mixture, in which a mixture of carbon monoxide and hydrogen with an H$_2$/CO molar ratio between 0.25 and 0.75 is contacted with a mixture of two catalysts of which one has the capability of catalyzing the conversion of an H$_2$/CO mixture into acyclic oxygen-containing hydrocarbons and the other is a catalyst according to the invention, and in which to the H$_2$/CO mixture an amount of water is added which, in %m based on the H$_2$/CO mixture, is at least 2.5 and at most $$\frac{3(V - R)}{(1 + R)(1 + V)},$$

wherein R = the H$_2$/CO molar ratio of the feed, and V = the consumption ratio of the H$_2$/CO mixture obtained under the conditions at which the above-mentioned process is carried out, but without water addition.

(12) A process for the preparation of a hydrocarbon mixture, in which a mixture of carbon monoxide and hydrogen with an H$_2$/CO molar ratio of less than 1.0 is contacted in a first step with a trifunctional catalyst combination containing one or more metal components with catalytic activity for the conversion of an H$_2$/CO mixture into acyclic hydrocarbons and/or acyclic oxygen-containing hydrocarbons, one or more metal components with catalytic activity for the water gas shift reaction, and silicalite, and in which at least the C$_2$$^-$ fraction of the reaction product from the first step is contacted in a second step with a catalyst containing one or more metal components with catalytic activity for the conversion of an H$_2$/CO mixture into acyclic hydrocarbons, which metal components have been chosen from the group formed by cobalt, nickel and ruthenium, on the understanding that, if the feed for the second step has an H$_2$/CO molar ratio of less than 1.5, water is added to this feed and in the second step a bifunctional catalyst combination is used which contains, in addition to the metal components with catalytic activity for the conversion of an H$_2$/CO mixture into acyclic hydrocarbons, also one or more metal components with catalytic activity for the water gas shift reaction.

The invention will now be explained with reference to the following example.

EXAMPLE

A sample of silicalite was successively calcined in air for three hours at 500° C., boiled with a 1.0 molar NH$_4$NO$_3$ solution (10 ml solution per gram silicalite), washed with water, dried at 120° C. and calcined in air for one hour at 500° C. The product thus obtained was divided into four portions and each of these portions was used in one of the four following catalytic experiments.

EXPERIMENT 1

A catalyst mixture was prepared by mixing a ZnO-Cr$_2$O$_3$ composite with silicalite. The atomic Zn-percentage of the ZnO-Cr$_2$O$_3$ composite, based on the sum of Zn and Cr, was 70%. The catalyst mixture contained per part by volume of silicalite 2.4 parts by volume of the ZnO-Cr$_2$O$_3$ composite. The catalyst mixture thus prepared was tested for the preparation in one step of the aromatic hydrocarbon mixture from an H$_2$/CO mixture. The test was carried out in a 50-ml reactor containing a fixed catalyst bed with a volume of 7.5 ml. An H$_2$/CO mixture with an H$_2$/CO molar ratio of 0.5 was conducted over the catalyst mixture for 48 hours at a temperature of 375° C., a pressure of 60 bar and a space velocity of 1000 l.l$^{-1}$.h$^{-1}$. The results of this experiment are given below:

| Average conversion of the synthesis gas: 50% v | |
|---|---|
| Average composition of the C$_1$$^+$ product, % w | |
| C$_1$ | 4 |
| C$_2$ | 6 |
| C$_3$ | 14 |
| C$_4$ | 5 |
| C$_5$$^+$ | 71 |
| Average composition of the C$_5$$^+$ product, % w | |
| acyclic hydrocarbons | 20 |
| naphthenes | 30 |
| aromatics | 50 |

EXPERIMENT 2

Silicalite was tested as catalyst for the preparation of an aromatic hydrocarbon mixture from dimethyl ether. The test was carried out in a 50-ml reactor containing a fixed catalyst bed with a volume of 7.5 ml consisting of a mixture of 1 ml silicalite and 6.5 ml alumina. Dimethyl either was conducted over the catalyst at 375° C., atmospheric pressure and a space velocity of 16.5 g dimethyl ether/g silicalite/h. The results of this experiment are given below:

Activity (%w of the dimethyl ether converted into hydrocarbons): 73

C$_5$$^+$ Selectivity (%w hydrocarbons on C$_1$$^+$ hydrocarbons in product): 69

%w aromatics in C$_5$$^+$ product: 52.

EXPERIMENT 3

Silicalite was tested as catalyst for the preparation of an aromatic hydrocarbon mixture from isobutylene.

The test was carried out in a 50-ml reactor containing a fixed catalyst bed with a volume of 5 ml consisting of silicalite. Isobutylene was conducted over the catalyst at 400° C., a pressure of 10 bar, a space velocity of 3.4 g isobutylene/g silicalite/h and an $H_2$/isobutylene molar ratio of 5:1. The result of this experiment is given below:

Aromatics selectivity (yield of aromatics in %w based on isobutylene feed): 20.

EXPERIMENT 4

A catalyst containing 2% w Zn on silicalite was prepared by impregnating silicalite with an aqueous solution of a Zn-salt followed by drying and calcining of the impregnated material. The Zn-silicalite thus prepared was tested as catalyst for the preparation of aromatic hydrocarbons from isobutane. The test was carried out in a 50-ml reactor containing a fixed catalyst bed with a volume of 5 ml consisting of Zn-silicalite. Isobutane was conducted over the catalyst at a temperature of 475° C., a pressure of 1.5 bar and a space velocity of 2 g isobutane/g silicalite/h. The results of this experiment are given below:

Activity =

$$\frac{pbw \text{ (overall product } - C_4 \text{ hydrocarbons in product)}}{pbw \text{ overall product}} \times 100 = 78$$

Aromatics selectivity =

$$\frac{pbw \text{ aromatic hydrocarbons in product}}{pbw \text{ (overall product } - C_4 \text{ hydrocarbons in product)}} \times 100 = 40.$$

We claim:

1. An aromatization process for preparing a hydrocarbon mixture of pentanes and higher and containing aromatics, which comprises contacting a feed selected from (1) gaseous mixtures containing carbon monoxide and hydrogen, (2) acyclic organic compounds selected from the group consisting of alcohols, ethers, olefins, diolefins, paraffins, aldehydes, ketones and esters, (3) aliphatic and/or cycloaliphatic hydrocarbon compounds and (4) mixtures of these in a contact zone at aromatization conversion conditions with a catalyst comprising as the sole siliceous component essentially alumina-free silicalite, and recovering a hydrocarbon product comprising aromatic compounds from said contact zone.

2. A process according to claim 1, wherein the feed consists of at least one compound selected from alcohols and ethers.

3. A process according to claim 2, wherein the feed comprises methanol and/or dimethyl ether.

4. A process according to claim 1, wherein said feed is selected from a $C_4^-$ monoolefin and a hydrocarbon mixture consisting of more than 75%w $C_4^-$ monoolefins.

5. A process according to claim 4, wherein said feed is a $C_3$ or $C_4$ monoolefin or a hydrocarbon mixture consisting substantially of one or more of these monoolefins.

6. A process according to claim 1, wherein said feed is a $C_4$ paraffin or a hydrocarbon mixture consisting of more than 75%w $C_4^-$ paraffins and of more than 50%w $C_4$ paraffins.

7. A process according to claim 1, wherein said feed comprises an $H_2$/CO mixture which feed is contacted in a first step with a catalyst containing one or more metal components with catalytic activity for the conversion of an $H_2$/CO mixture into acyclic hydrocarbons and/or acyclic oxygen-containing hydrocarbons, followed by converting the product thus obtained in the second step into hydrocarbon mixture containing aromatic compounds by contacting it under aromatization conditions with silicalite.

8. A process according to claim 1, wherein said feed comprises an $H_2$/CO mixture, which is contacted with a bifunctional catalyst containing, in addition to silicalite, one or more metal components with catalytic activity for the conversion of an $H_2$/CO mixture into acyclic hydrocarbons and/or acyclic oxygen-containing hydrocarbons and a hydrocarbon mixture containing aromatics is recovered.

9. A process according to claim 1, wherein said feed is an $H_2$/CO mixture with an $H_2$/CO molar ratio of less than 1.0, is contacted in a single step under aromatization conditions with a trifunctional catalyst containing one or more metal components with catalytic activity for the conversion of an $H_2$/CO mixture into acyclic hydrocarbons and/or acyclic oxygen-containing hydrocarbons, one or metal components with catalytic activity for the water gas shift reaction, and silicalite and a hydrocarbon mixture containing aromatics is recovered.

10. A process according to claim 9, wherein of the reaction product at least the $C_2^-$ fraction is further contacted in a step with a catalyst containing one or more metal components with catalytic activity for the conversion of an $H_2$/CO mixture into acyclic hydrocarbons, which metal components are selected from the group consisting of cobalt, nickel and ruthenium.

11. A process according to claim 9, wherein the trifunctional catalyst is composed of two separate catalysts, of which one catalyst (catalyst X) contains the metal components with catalytic activity for the conversion of an $H_2$/CO mixture into substantially oxygen-containing hydrocarbons and with catalytic activity for the water gas shift reaction, and the other catalyst (catalyst y) is silicalite.

12. A process according to claim 11, wherein the X-catalyst is capable of converting an $H_2$/CO mixture into substantially methanol and/or dimethyl ether.

13. A process according to claim 12, wherein the X-catalyst contains the metal combination zinc-chromium.

14. A process according to claim 8 or 9, wherein the contacting of the $H_2$/CO mixture in said contact zone is carried out at a temperature of from 200° to 500° C., a pressure of from 1 to 150 bar and a space velocity of from 50 to 5000 Nl gas/l catalyst/h.

* * * * *